United States Patent [19]

Bundy

[11] 4,251,463

[45] Feb. 17, 1981

[54] 2-DECARBOXY-2-AMINOMETHYL-9-DEOXY-9-METHYLENE-5,6-DIDEHYDRO-PGF$_1$ COMPOUNDS

[75] Inventor: Gordon L. Bundy, Portage, Mich.

[73] Assignee: The Upjohn Company, Kalamazoo, Mich.

[21] Appl. No.: 115,967

[22] Filed: Jan. 28, 1980

Related U.S. Application Data

[62] Division of Ser. No. 35,144, May 1, 1979.

[51] Int. Cl.$^3$ .......................................... C07C 87/451
[52] U.S. Cl. ...................................................... 564/454
[58] Field of Search ................. 260/563 R, 570.5 CA, 260/574

[56] References Cited

U.S. PATENT DOCUMENTS

| 3,849,474 | 11/1974 | Abraham et al. | 260/584 A X |
| 3,919,285 | 11/1975 | Axen | 560/121 |
| 3,935,240 | 1/1976 | Mallion | 260/571 X |
| 3,954,741 | 5/1976 | Schaaf et al. | 260/561 R X |
| 4,064,351 | 12/1977 | Sukai et al. | 260/574 X |

FOREIGN PATENT DOCUMENTS 2635985  2/1978  Fed. Rep. of Germany ........... 560/121

OTHER PUBLICATIONS

Johnson, "JACS", 100, pp. 7690–7704, (1978).

*Primary Examiner*—John Doll
*Attorney, Agent, or Firm*—Robert A. Armitage

[57] ABSTRACT

The present invention particularly relates to novel 2-decarboxy-2-aminomethyl-9-deoxy-9-methylene-5,6-didehydro-PGF$_1$ compounds and methods for their preparation in pharmacological use.

2 Claims, No Drawings

2-DECARBOXY-2-AMINOMETHYL-9-DEOXY-9-METHYLENE-5,6-DIDEHYDRO-PGF$_1$ COMPOUNDS

DESCRIPTION

CROSS REFERENCE TO RELATED APPLICATIONS

The present application is a divisional application of U.S. Ser. No. 035,144, filed May 1, 1979, now pending.

BACKGROUND OF THE INVENTION

The present invention particularly relates to novel 2-decarboxy-2-aminomethyl-9-deoxy-9-methylene-5,6-didehydro-PGF$_1$ compounds and methods for their preparation and pharmalogical use.

The essential material constituting the disclosure of the preparation and pharmacological use of the compounds of the present invention is incorporated here by reference from U.S. Ser. No. 035,144 and U.S. Pat. No. 4,060,534. The latter patent describes certain 9-deoxy-9-methylene-PGF-type compounds which are cis isomers of the novel compounds disclosed herein.

PRIOR ART

Known in the art are trans-5,6-didehydro PG$_1$ compounds and 9-deoxy-9-methylene PGF compounds. Trans-5,6-didehydro prostaglandins are described in U.S. Pat. Nos. 3,759,978, 3,823,180, 3,832,379, and 3,821,291.

SUMMARY OF THE INVENTION

The present invention particularly provides:
a prostaglandin analog of formula VI

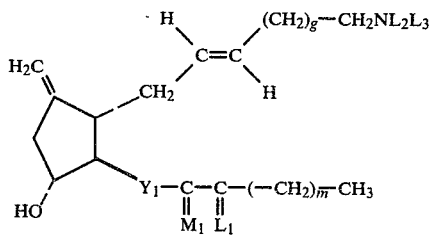

wherein Y$_1$ is trans—CH=CH—, —C≡C—, —CH$_2$CH$_2$—, or cis—CH=CH—;
wherein M$_1$ is α—R$_5$:β—OH or α—OH:β—R$_5$, wherein R$_5$ is hydrogen or methyl;
wherein L$_1$ is α—R$_3$:β—R$_4$, α—R$_4$:β—R$_3$, or a mixture of α—R$_3$:β—R$_4$ and α—R$_4$:β—R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5; wherein m is one to 5, inclusive; and
wherein L$_2$ and L$_3$ are hydrogen or alkyl of one to 4 carbon atoms, inclusive, being the same or different, or a phramcologically acceptable acid addition salt thereof.

DESCRIPTION OF THE PREFERRED EMBODIMENTS

The present invention particularly relates to the following specific embodiment:
2-decarboxy-2-hydroxymethyl-5,6-trans-didehydro-9-deoxy-9-methylene-16,16-dimethyl-PGF$_1$.

I claim:

1. A prostaglandin analog of formula VI

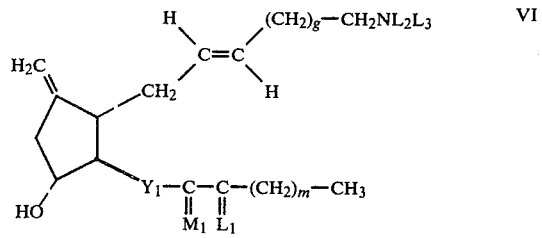

wherein Y$_1$ is trans—CH=CH—, —C≡C—, —CH$_2$CH$_2$—, or cis—CH=CH—;
wherein M$_1$ is α—R$_5$:β—OH or α—OH:β—R$_5$, wherein R$_5$ is hydrogen or methyl;
wherein L$_1$ is α—R$_3$:β—R$_4$, α—R$_4$:β—R$_3$, or a mixture of α—R$_3$:β—R$_4$ and α—R$_4$:β—R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5; wherein m is one to 5, inclusive; and
wherein L$_2$ and L$_3$ are hydrogen or alkyl of one to 4 carbon atoms, inclusive, being the same or different, or a phramcologically acceptable acid addition salt thereof.

2. 2-Decarboxy-2-aminomethyl-5,6-trans-didehydro-9-deoxy-9-methylene-16,16-dimethyl-PGF$_2$, a prostaglandin analog according to claim 1.

* * * * *

UNITED STATES PATENT OFFICE
CERTIFICATE OF CORRECTION

Patent No. 4,251,463     Dated  17 February 1981

Inventor(s)  Gordon L. Bundy

It is certified that error appears in the above-identified patent and that said Letters Patent are hereby corrected as shown below:

In Related U.S. Application Data: "Ser. No. 35,144, May 1, 1979" should read -- Ser. No. 35,144, May 1, 1979, now U.S. Patent 4,220,796 --;

Column 1, line 11, "now pending" should read -- now U.S. Patent 4,220,796 --.

*Signed and Sealed this*

*Twenty-sixth* Day of  *May 1981*

[SEAL]

*Attest:*

RENE D. TEGTMEYER

*Attesting Officer*     *Acting Commissioner of Patents and Trademarks*